United States Patent [19]

Asbjornsen

[11] Patent Number: 4,842,417
[45] Date of Patent: Jun. 27, 1989

[54] METHOD AND APPARATUS FOR INDIRECTLY MEASURING A SOLID-LIQUID INTERFACE EQUILIBRIUM TEMPERATURE

[75] Inventor: Odd A. Asbjornsen, Arnold, Md.

[73] Assignee: Norsk Hydro A.S., Oslo, Norway

[21] Appl. No.: 230,698

[22] Filed: Aug. 9, 1988

Related U.S. Application Data

[63] Continuation-in-part of Ser. No. 69,528, Jul. 1, 1987, abandoned.

[51] Int. Cl.$^4$ ..................... G01K 13/00; G01K 11/00
[52] U.S. Cl. ..................... 374/139; 374/163; 374/43; 374/29; 374/7
[58] Field of Search ............... 374/100, 101, 139, 163, 374/165, 29, 7, 43, 44; 364/557

[56] References Cited

U.S. PATENT DOCUMENTS

| | | | |
|---|---|---|---|
| 3,134,848 | 3/1964 | Musial | 374/29 |
| 3,333,470 | 8/1967 | Fingerson | 374/29 |
| 3,462,997 | 8/1969 | Roach et al. | 374/7 |
| 3,490,283 | 1/1970 | Vidal et al. | 374/163 |
| 3,624,709 | 11/1971 | Petrek | 374/7 |
| 3,918,303 | 11/1975 | Zakhidov et al. | 374/29 |
| 4,358,957 | 11/1982 | Lougheed et al. | 374/165 |

FOREIGN PATENT DOCUMENTS 2131175 6/1984 United Kingdom ............... 374/43

Primary Examiner—William A. Cuchlinski, Jr.
Assistant Examiner—Thomas B. Will
Attorney, Agent, or Firm—Wenderoth, Lind & Ponack

[57] ABSTRACT

A method and apparatus for indirectly measuring the solid-liquid interface equilibrium temperature dynamically excites the heat flux flowing through a coldfinger arrangement followed by a statistical estimation of the interface temperature, solid layer heat conductivity and thickness ratio, bulk liquid temperature and thermal heat transfer coefficient. The coldfinger includes a pair of substantially concentric and substantially cylindrical members arranged one within another so as to have an outer member and a venturi-shaped inner member and a space therebetween. The members are arranged such that a gas flows through the inner member and a space between the inner and outer members of the coldfinger and then exits the coldfinger arrangement. The average gas temperature within the space of the coldfinger and the difference in temperature between the gas entering the coldfinger and the gas exiting the coldfinger are measured and the heat flux flowing through the coldfinger is varied in a time varying fashion either by varying the amount of heat supplied to the gas entering the coldfinger or by varying the amount of gas flowing through the coldfinger. The solid-liquid interface equilibrium temperature is determined on the basis of the respective measured temperatures and the specific parameters of the gas and the solid and the liquid and the gas flowrate and the dimensions of the coldfinger.

16 Claims, 4 Drawing Sheets

METHOD AND APPARATUS FOR INDIRECTLY MEASURING A SOLID-LIQUID INTERFACE EQUILIBRIUM TEMPERATURE

This application is a continuation-in-part, of now abandoned application Ser. No. 069,528, filed July 1, 1987.

BACKGROUND OF THE INVENTION

The present invention is directed to a method and apparatus for indirectly measuring the solid-liquid interface equilibrium temperature by the dynamic excitation of the heat flux flowing through a "coldfinger" arrangement followed by a statistical estimation of the interface temperature, solid layer heat conductivity and thickness ratio, bulk liquid temperature and thermal heat transfer coefficient.

The aluminum industry would find it very valuable to have an accurate technique for determining, in real time, the cryolite liquid temperature, concentration of alumina, and bath temperature during the operation of an aluminum reduction cell. Such measurements could be used to control the operation of the aluminum reduction cell so as to optimize its operation and reduce the amount of energy needed.

Direct measurements of the various temperatures in the aluminum reduction cell are possible. However, the high temperatures involved and corrosive properties of the molten cryolite liquid require the use of expensive temperature measuring devices (e.g.—specially cladded thermocouples) having short lifetimes.

In view of the fact that other operational parameters in an aluminum reduction cell have been successfully estimated using simple mathematical models and on-line parameter estimation (e.g.—the ohmic resistance of the cryolite bath and the effective interelectrode gap), the present invention has been developed specifically for the accurate on-line estimation of the liquid temperature, alumina concentration, and average temperature of the cryolite bath. The invention is, of course, also applicable to other analogous molten bath situations, or solid-liquid equilibrium phenomena.

The alumina concentration of the cryolite bath can be estimated using a cryolite phase diagram with constant composition of all additives except alumina and an accurate estimate of the cryolite solid-liquid interface temperature. The basis of the interface temperature estimation is the observation of the dynamic heat transfer from the cryolite bath through a layer of frozen cryolite. This heat transfer is excited through the use of a "coldfinger" arrangement.

The coldfinger thermometer pocket excites the heat transfer from the bath through a layer of frozen cryolite and a tube wall to a gas flowing through the coldfinger. Excitation is accomplished by a periodic fluctuation of the inlet gas temperature and/or flowrate.

The inlet and exit temperatures of the gas are monitored using standard thermocouples.

Since the standard thermocouples are only subjected to the gas flowing through the coldfinger, expensive corrosion resistant devices with short lives are not needed.

SUMMARY OF THE INVENTION

A method and apparatus for indirectly measuring the solid-liquid interface equilibrium temperature utilizes the dynamic excitation of the heat flux flowing through a coldfinger followed by the statistical estimation of the interface temperature, solid layer heat conductivity and thickness ratio, bulk liquid temperature, and thermal heat transfer coefficient.

The coldfinger consists of a cylindrical arrangement including a venturi-shaped inner hollow cylinder and an outer cylinder. Air, or some other gas, is directed into the venturi-shaped inner hollow cylinder through an air nozzle and is exhausted out through the outer cylinder.

The temperature of the exhausted air and the differential temperature between the input air and the exhausted air are measured. In addition, a heating device is placed in the path of the input air ahead of the air nozzle and either the heater is operated intermittently or the air flow varied as a function of time so as to cause the dynamic excitation of the heat flux flowing through the coldfinger.

In another embodiment, the coldfinger consists of a closed hollow outer cylindrical cylinder and an open hollow cylindrical cylinder of a smaller diameter which is placed within the outer cylinder. Air or some other gas is directed into the inner hollow cylinder and is then exhausted through the outer cylinder. Temperature measurements are made at the input to the inner cylinder and at the output of the outer cylinder and at an intermediate point corresponding to the outlet of the inner cylinder and the inlet of the outer cylinder.

The various temperatures and the heat transfer coefficient are then determined from the two measured temperatures and the known parameters of the materials and the coldfinger.

DESCRIPTION OF THE PREFERRED EMBODIMENT

Figure 1:
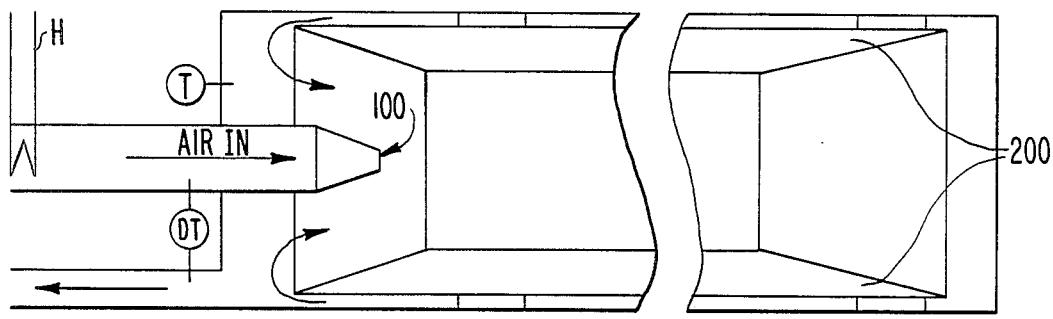
FIG. 1 illustrates a coldfinger arrangement in accordance with the present invention.

Referring to FIG. 1, the air, after being heated by heater H, passes through a central nozzle 100, reaching a velocity of about $Ma=1$, whereby air is sucked from the outer annulus (which consists of a venturi-shaped body which is hollow to reduce thermal inertia) 200 to the central core. This makes it possible to obtain almost perfect mixing conditions in the interior air chamber of the coldfinger, exposing the inner wall temperature to roughly the same temperature, and maintaining a very high heat transfer coefficient for cooling between the inner wall and the air. The air flow through the apparatus is assumed to be constant, but could be varied as a function of time instead of varying the heat excitation as noted below.

Figure 1A:
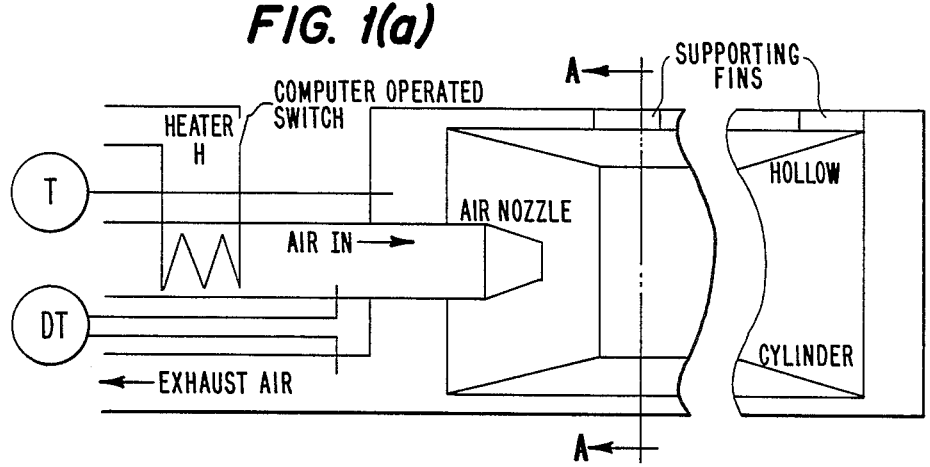
FIG. 1(a) illustrates the coldfinger of FIG. 1 in slightly greater detail and FIG. 1(b) illustrates a cross-sectional view of FIG. 1(a) through plane A—A.
Figure 1B:
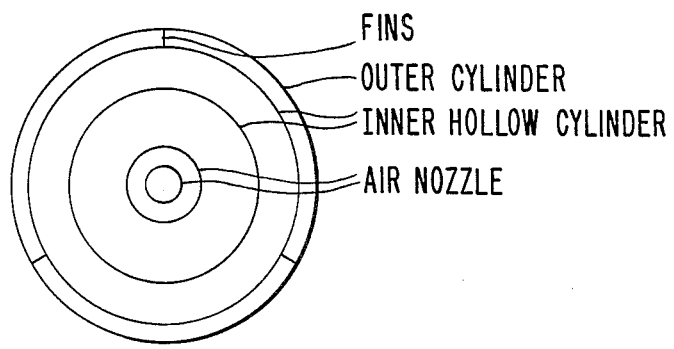

In greater detail, FIGS. 1(a) and 1(b) illustrate the coldfinger device in greater detail, FIG. 1(b) being a cross-sectional view of FIG. 1(a) taken through plane A—A.

There are two absolute and one differential temperature measurements. The absolute temperature measurement, by the temperature measuring device (e.g.—thermocouple) T, serves to identify the average air temperature in the mixing chamber, while the temperature difference measurement, by the temperature measuring device DT, serves to identify the heat picked up by the air in the mixing chamber. An important consideration in the design of the instrument, is to make sure that the thermocouples for these measurements are not exposed to too high temperatures. A typical safe range may be 500°–600° C., or 800–900 K. This may be adjusted by the average air flow, as indicated below.

The switch controlling the heater H and the two thermocouples (or other temperature measuring devices) T and DT are both interfaced with any commercially available computer utilizing commercially available computer interfaces, for example, those disclosed in detail in Data Acquisition and Computer Interface Handbook and Encyclopedia, published by Omega Engineering, Inc.

Figure 1C:
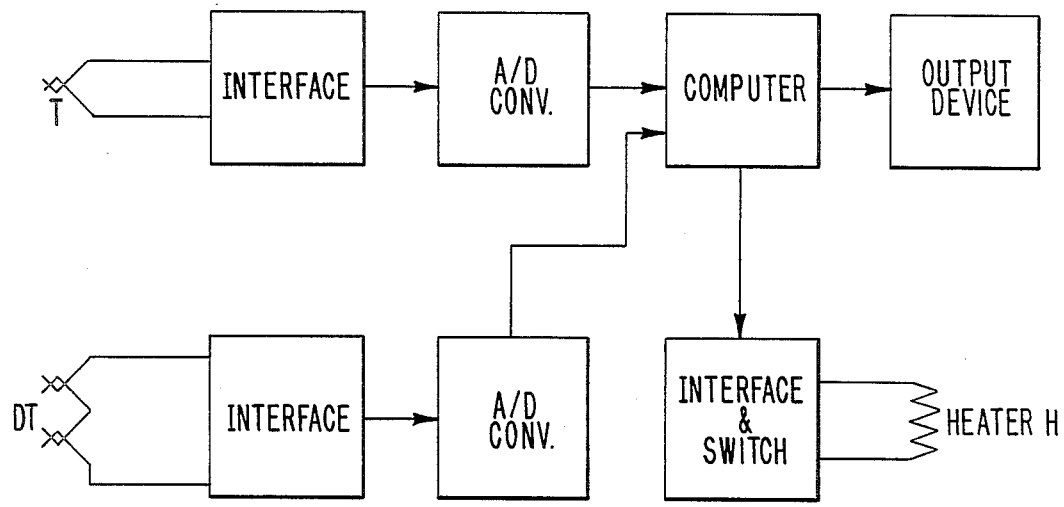
FIG. 1(c) illustrates a block diagram of the electrical arrangement in accordance with the present invention.

FIG. 1(c) illustrates the electrical arrangement in accordance with the present invention.

Thermocouples T and DT are respectively connected to commercially available interfaces which are in turn respectively connected to commercially available A/D converters which are in turn connected to a commercially available computer.

It is noted that Omega Engineering, Inc. manufactures combination plug-in interface—A/D converter cards for many of the commercially available personal computers, such as the IBM PC computers, for example.

The computers is in turn connected to a commercially available interface and switch which is used to power the heater H and is also connected to an output device which may be a printer or CRT screen, etc.

The average amount of air flow required for the cooling may be calculated from an anticipated cryolite layer thickness, the heat flow through this layer, and the temperature rise of the air:

$$G = q/(c_p \Delta T) = (k/\delta)(T_s - T_c)/(c_p(T_c - T_g)) \quad (1)$$

The heater H should be able to increase the air temperature, say by 100° C., at the flowrate specified. With a heat capacity of about 0.34 kcal/kg°C. for air, this requires a heater power of roughly 0.8 to 1 kW, about the same as a standard hair-blower. The heater elements should preferably be bare wires, as in a commercially available hairdryer, and located as near as practically possible to the air inlet to the coldfinger. This is in order to avoid heat loss and attenuation of the temperature fluctuations. Apart from this, the design of the heater is not critical. The design of a commercially available hairdryer may serve as a guideline. The heater has an on-off relay operated by a computer.

Using the following previously obtained data:
$k = 1.19$ Watt/(m K.), $d = 2$ mm, $T_s = 1200$ K., $c_p = 1117$ J/kg, $T_g = 300$ K., $T_c = 800$–900 K.,
results in a calculated typical range of specific gas flowrates per unit of exposed area of the coldfinger:

Maximum:
$G_s = (1.19/0.002)*(400)/(1117*(500)) = 0.426$ kg/(sec m$^2$)

Minimum:
$G_s = (1.19/0.002)*(300)/(1117*(600)) = 0.266$ kg/(sec m$^2$) $\quad (2)$ Choosing an inner coldfinger diameter of 25 mm and an effective length of 150 mm, results in a heat transfer surface of A = 117.8 cm$^2$. Then the range of required air flowrates for cooling would be roughly:

Maximum: $G = G_s A = 0.426*0.01178 = 0.00502$ kg/sec = 18.07 kg/hr.

Minimum: $G = G_s A = 0.266*0.01178 = 0.00313$ kg/sec = 11.28 kg/hr. $\quad (3)$ The temperature at the nozzle may be 500—600 K., leading to an air density of 0.6—0.7 kg/m$^3$ and a sonic velocity in the range 467—426 m/sec. Assuming that the air velocity in the nozzle outlet will be roughly sonic, then the range of required nozzle diameters will be:

Maximum:
$d = [4G/(\pi v_n \rho)]^{\frac{1}{2}} = [0.00502*4/(\pi*426*0.6)]^{\frac{1}{2}} = 5.0$ mm Minimum:
$d = [4G/(\pi v_n \rho)]^{\frac{1}{2}} = [0.00313*4/(\pi*467*0.7)]^{\frac{1}{2}} = 3.5$ mm $\quad (4)$ At a sonic velocity in the nozzle, the pressure before the nozzle has to be about twice that of atmospheric pressure, giving a pressure ratio of about 0.5 per FIG. 6-68 of the Chemical Engineers Handbook by Chilton, McGraw-Hill, 1976. Assuming that the diameter of the mixing section of the ejector will be $d_m = 15$ mm, then the area ratio between the cross-section of the mixing section and the nozzle per the aforecited FIG. 6-68, may vary from $(15/5)^2 = 9$, to $(15/3.5)^2 = 18.4$. Assume that the thickness of the outer annulus is a = 2 mm. According to FIG. 6-68 noted above, it is reasonable to anticipate a ratio R of the recycle rate on the order of 1–2, as a very conservative estimate. At the mixing chamber temperature, the air density will be roughly p = 0.45–0.4 kg/m$^3$, which means that the air velocity in the annulus of the mixing chamber could vary between:

Maximum: $v_a = 2RG/(\rho a(d_m + d)\pi) =$ $\quad (5)$ $(2*0.00502/(0.45*0.002*0.023*\pi) = 154$ m/sec.

Minimum: $v_a = 2RG/(\rho a(d_m + d)\pi) =$ $(1*0.00313/(0.4*0.002*0.023*\pi) = 54$ m/sec.

This result indicates that very good mixing effect will be obtained with the proposed design, and also that a good heat transfer between the gas and the wall is quite reasonable. It also makes it possible to avoid the manipulation of the air flowrate, but rather to manipulate the gas inlet temperature by a simple bare wire electric heater, and measure the air heat uptake at constant air mass velocity, as indicated in FIG. 1.

The conclusion drawn above is conservative, because one may allow a pressure drop in the annulus corresponding to a pressure ratio of 0.5 (i.e.—a pressure drop equal to 0.5 bar), and still have a pressure ratio between the inlet air and recycle air entering the ejector, of about 0.25. According to the aforecited FIG. 6-68, this will still hold for the calculations carried out above and the results will still be within the limits indicated in terms of the recycle ratio. Therefore, it is reasonable to conclude, that the mixing chamber design illustrated in FIG. 1, will satisfy the simplifying assumptions made for the parameter estimation below.

As long as the solid thickness of cryolite crust is small, relative to the coldfinger diameter, the heat dynamics of the crust may be simplified to that of a flat plate. Otherwise, the partial differential operator of the heat dynamics must comply with cylindrical coordinates. This introduces only formal complications, and does not affect the principle of the modeling methods. In order to simplify the explanation of the basic principles of the estimation routine following the application of the invention, the flat plate geometry is used.

If the heat flux variations, caused by the excitation of the dynamic heat balance of the coldfinger, are reasonably fast relative to the melting of the crust, one may also assume that the crust layer thickness does not change, but remains fairly constant at an average level. If the crust thickness is allowed to vary significantly, say by a low frequency excitation, the parameter estimation problem becomes a nonlinear one. In the following discussion, only the case of the constant crust-layer thickness is considered.

Figure 2:
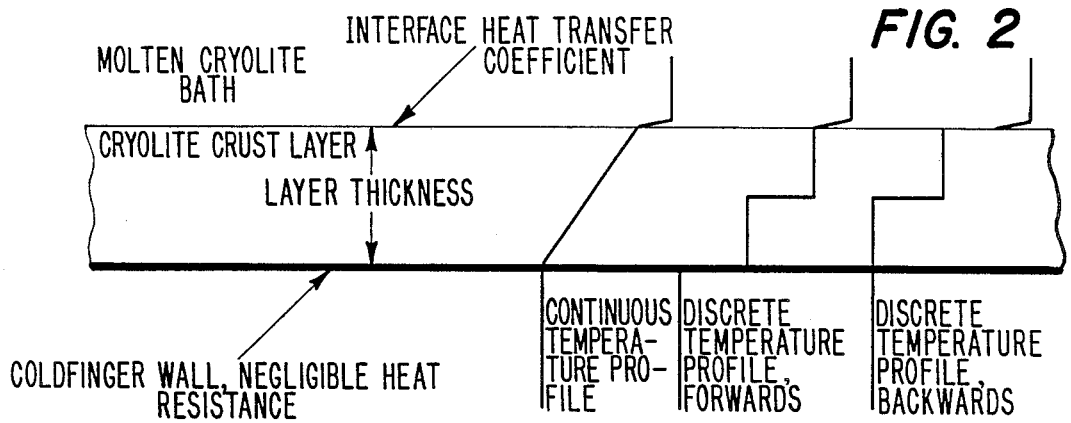
FIG. 2 illustrates a simplified schematic diagram of the heat transfer through the crust formed outside of the coldfinger wall.

The steady state temperature profile is shown in FIG. 2. In a transient mode, the profile is discretized by a partitioning of the crust into parallel layers. In FIG. 2, two such layers are shown with forward and backwards differences respectively. The forward difference scheme is used with the assumption of a constant layer thickness, an assumption which is reasonable when the rate of change of the air temperature is in a range that does not affect the thickness of the layer in any appreciable way.

The model for a constant layer thickness is extremely simple, when divided into discrete layers. In FIG. 2 two layers are portrayed as a discrete temperature profile. This is an approximation, but practical experiments would reveal if there are sufficient information in the temperatures and the temperature differences to justify a more detailed partitioning of the crust layer. The dynamics of the heat transfer and heat diffusion would then be approximated by a system of first order time differential equations:

Heat balance for layer 1, with an average temperature of $T_1$:

$$dT_1/dt = [2h_m/(\rho c_p \delta)](T_m - T_1) - [4k/(\delta^2 \rho c_p)](T_1 + T_2) \quad (6)$$

where $\delta$ is the total thickness of the cryolite layer, $h_m$ the heat transfer coefficient between cryolite melt and the crust, $(\rho c_p)$ is the specific volume heat capacity of the crust, and $k$ its heat conductivity.

Heat balance for layer 2, with an average temperature of $T_2$:

$$dT_2/dt = [4k/(\delta^2 \rho c_p)](T_1 - T_2) - [2h_g/(\rho c_p \delta)](T_2 + T_3) \quad (7)$$

Heat balance for the air mixing stage, with an average temperature of $T_3$:

$$dT_3/dt = [h_g/C](T_2 - T_3) - [Gc_g/C](T_3 - T_i) \quad (8)$$

where C is the effective capacity of the mixing stage, with its interior, and $c_g$ is the specific heat capacity of air. The heat transfer coefficient from the wall to the air is $h_g$, and G is the gas flowrate. The inlet gas temperature, subject to excitation, is $T_i$.

Euler integration of those equations over the sampling time interval, say interval no.k, gives:

$$T_1(k) = a_1 T_m(k-1) + \quad (9)$$
$$(1 - a_1)T_1(k-1) - a_2(T_1(k-1) - T_2(k-1))$$

$$T_2(k) = a_2 T_1(k-1) + (1 - a_2 - a_3)T_2(k-1) + a_3 T_3(k-1) \quad (10)$$

$$T_3(k) = a_3 T_2(k-1) + (1 - a_3)T_3(k-1) + b_1 \Delta T_i(k-1) \quad (11)$$

Here are, $\Delta T_i$ the measured temperature difference $T_i - T_3$, and:

$$a_1 = 2h_m/(\rho c_p \delta);\ a_2 = 4k/(\delta^2 \rho c_p);\ a_3 = 2h_g/(\rho c_p \delta);\ b_1 = [Gc_g/C]; \quad (12)$$

Over one sampling time interval, the molten salt temperature may be considered constant, and can be eliminated from the equations by considering incremental values in equation (9):

$$T_1 = (k)T_1(k-1) = (1-a_1)(T_1(k-2))$$
$$-a_2[(T_1(k-1) - T_1(k-2)) - (T_2(k-1) - T_2(k-2))] \quad (13)$$

Introduce the parameters $c_1$, $c_2$, and $c_3$:

$$c_1 = 1 - a_1 - a_2;\ c_2 = 1 - a_2 - a_3;\ c_3 = 1 - a_3; \quad (14)$$

Elimination of the intermediate temperatures by the backwards shift operator, gives a third order Auto-Regression equation of the form:

$$T_3(k) = \alpha_1 T_3(k-1) + \alpha_2 T_3(k-2) + \alpha_3 T_3(k-3)$$
$$+ \beta_1 \Delta T_i(k-1) + \beta_2 \Delta T_i(k-2) + \beta_3 \Delta T_i(k-3) \quad (15)$$

The ARMA (Auto-Regression Moving Average) model has six parameters, while the original problem had only four. Hence, the back calculation to the original parameters from the ARMA model parameters is an over-determined system of equations, where the coefficients are:

$$\alpha_1 = c_1 + c_2 + c_3 = 3 - a_1 - 2a_2 - 2a_3 \quad (16)$$

$$\alpha_2 = a_2^2 + a_3^2 + c_1 c_2 + c_1 c_3 + c_2 c_3 =$$
$$-3 + 2a_1 + 4a_2 + 4a_3 - a_1 a_2 - 2a_1 a_3 - 3a_2 a_3$$

$$\alpha_3 = c_1 c_2 c_3 - a_2^2 c_3 - a_3^2 c_1 - 1 - a_1 - 2a_2 -$$
$$2a_3 + 2a_1 a_3 + 3a_2 a_3 - a_1 a_2 a_3$$

$$\beta_1 = b_1$$

$$\beta_2 = b_1(c_1 + c_2) = b_1(2 - a_1 - 2a_2 - a_3)$$

$$\beta_3 = b_1(c_1 c_2 - a_2^2) =$$
$$b_1(1 - a_1 - 2a_2 - a_3 + a_1 a_2 + a_1 a_3 + a_2 a_3)$$

An approach to this problem, would be to determine the coefficients from the six relationships, by a least sum of squares of the residuals. This minimization will be a nonlinear programming problem, since the a- and b-parameters enter the relationships in a nonlinear way.

If the new parameters are organized in a parameter vector p:

$$p^T = [\alpha^T, \beta^T] = [\alpha_1, \alpha_2, \alpha_3, \beta_1, \beta_2, \beta_3] \quad (17)$$

Then, the model becomes a linear single input, single output, ARMA model in terms of the outlet temperature measurement $T_3$, the inlet temperature measurement $T_i$, the backwards shift operator E and the parameter vector p:

$$T_3(k) = p_1 T_3(k-1) + p_2 T_3(k-2) + p_3 T_3(k-3) \\ + p_4 \Delta T(k-1) + p_5 \Delta T(k-2) + p_6 \Delta T(k-3) \quad (18)$$

where the new parameters are as explained above.

The six parameters in equation (18) are calculated by a standard least square regression procedure, given in most textbooks in estimation. See, for example, Dynamic System Identification: Experiment Design and Data Analysis Goodwin, G. C. and R. L. Payne, Academic Press (1977). In the present method suggested here, a fixed window of observations is considered, say a few periods of the input excitation of the temperature. Within this window are N samples collected. Then, the least square estimator of the parameters may be written:

$$p = (X^T X)^{-1} X^T y \quad (19)$$

The elements of the vector y are:

$$\{y_i\} = T_3(k-i+1); \; i=1 \text{ to } N \quad (20)$$

The Matrix X is composed of the columns $x_i$: $X = [x_1, x_2, x_3, x_4, x_5]$, where the elements of each of those column vectors are:

$$x_1 = \{T_3(k-i)\}; \; x_2 = \{T_3(k-i-1)\}; \\ x_3 = \{T_3(k-i-2)\};$$

$$x_4 = \{\Delta T(k-i)\}; \; x_5 = \{\Delta T(k-i-1)\}; \\ x_6 = \{\Delta T(k-i-2)\}; \quad (21)$$

The vector y and the matrix X move along with the sampling number k, in a fixed size circular buffer. The parameter estimation is effected by sequential, partial regression techniques. Only the terms and parameters that have statistical significance are updated. At any point in the time series of parameters p, the updated elements of the parameter vector may be used to calculate the real physical parameters, according to the procedure:

$$\partial (p(q)^T p(q))/\partial q = 0; \text{ or equivalently: } p(q)^T \partial p(q)/\partial q = 0 \quad (22)$$

where the vector of original physical parameters $q^T = [h_m, h_g, \delta, k, Gc_g/C]$. The five parameters in the vector q are, the molten salt heat transfer coefficient: $h_m$, the air heat transfer coefficient: $h_g$, the crust thickness: $\delta$, the crust heat conductivity: k, and the "heat space velocity" in the air mixing chamber: $Gc_g/C$.

Once the p- and q-parameters are determined the back calculation to the parameters in the difference equations and some of the physical state variables, as, for example, the bath and the crust layer temperatures is relatively trivial:

The inner layer temperature (facing the air flow):

$$T_2(k-1) = [T_3(k) - (1-a_3)T_3(k-1) - b_1 \Delta T(k-1)]/a_3 \quad (23)$$

The outer surface layer temperature (facing the molten salt):

$$T_1(k-2) = [T_2(k-1) - (1-a_2-a_3)T_2(k-2) - a_3 T_3(k-2)]/a_2 \quad (24)$$

The molten salt temperature:

$$T_m(k-3) = [T_1(k-2) - (1-a_1-a_2)T_1(k-3) + a_2 T_2(k-1)]/a_1 \quad (25)$$

In order to increase the accuracy of the estimated physical parameters, one may divide the crust into more layers. This will not reveal any other parameters, but the apparent order of the ARMA model will increase the number of ARMA model parameters, and hence the dimension of p. This leaves more terms in the sum of squares to be minimized by the q-parameters. The relationship between the apparent dimension of p and the number of layers is:

$$\dim(p) = 2(n+1); \; n = \text{number of layers} \quad (26)$$

It should be emphasized, that the larger n is, the more difficult it will be to determine the coefficients in p, because of the danger of over-fitting. This may be circumvented by a direct nonlinear parameter estimation from the ARMA model, applied to the physical parameters directly. One would then write the least square criterion over the observation window:

$$e^2 = (y^T - p^T X^T)(y - Xp) \quad (27)$$

and solve the set of equations below with respect to the physical parameter set q:

$$(\partial p(q)/\partial q)^T X^T y - (\partial p(q)/\partial q)^T X^T X p(q)) = 0 \quad (28)$$

by any iterative procedure, for example, by a Newton-Raphson method.

Figure 4:
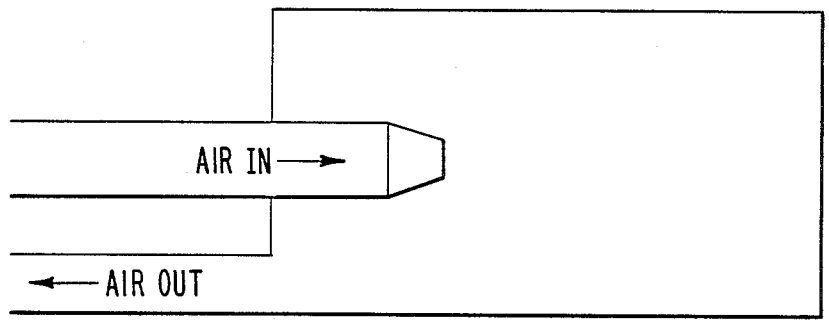
FIG. 4 illustrates a simplified coldfinger for use in accordance with the present invention.

FIG. 4 illustrates a simplified coldfinger for use in accordance with the present invention.

Essentially, the coldfinger of FIG. 4 corresponds to that illustrated in FIGS. 1(a) and 1(b) except for the elimination of the inner hollow cylinder.

By appropriately designing the air nozzle and cylinder dimensions, it is possible to provide sufficient air circulation so as to have a reasonable thermoequilibrium within the cylinder without requiring the additional inner hollow cylinder of the previously discussed embodiment.

In conclusion, an air-cooled hollow cylinder, a "coldfinger", is designed for indirect measurement of the bulk temperature of a fluid phase, in equilibrium with a precipitated solid, for example a frozen crust-layer on the surface of the "coldfinger", as well as the surface temperature of the "coldfinger" crust-layer in the fluid, by a dynamic excitation of the heat balance of the heat transfer and heat diffusion, and a mathematical model describing those dynamics. From this model, a statistical parameter identification procedure may be applied to reveal the unknown physical variables, liquid bulk temperature, surface temperature, and heat transfer coefficient, at the solid liquid interface, as well as the crust-layer heat conductivity and thickness ratio.

The coldfinger is cooled from the interior by an air flow, facilitating the formation of a layer of solid (the crust-layer) on the surface of the coldfinger, by freezing. The frozen crust-layer protects the coldfinger from eventual corrosion from the liquid bath. The physical variables in question are basically the two mentioned temperatures and some transport properties and capacities. A particular feature is that the air flow rate need not be measured as long as the heat capacities of the air are well known.

The air flow into the coldfinger is driving an ejector for efficient air mixing of the air inside the hollow cylinder, facilitating near homogeneous temperature throughout the cylinder.

The inflowing air is heated in a cyclic fashion to reveal a cyclic dynamic response in the outlet temperature or temperature difference between inlet and outlet. The air temperature measurements are accomplished by simple thermocouples, or resistance thermometers, and the inlet temperature excitation is accomplished by a computer operated power switch for an electric resistance heater.

The time variations in the inlet and outlet temperatures are used to estimate the parameters in an ARMA model (Auto Regression Moving Average model), from which the molten phase temperature, the crust skin temperature, the fluid phase heat transfer coefficient, the ratio between the heat conductivity of the frozen layer (the crust) and its thickness, the air phase heat transfer coefficient, as well as the ratio between the air flow mass velocity and the thermal inertia of the coldfinger.

The thermal dynamics of the coldfinger are modeled by a simple discretization of the partial differential equation for heat diffusion, with the interface heat transfers as boundary condition, leading to a standard ARMA model for the time series, where the model contains information about the unknown state variables and parameters. The parameters are determined by a standard least square regression analysis, known as the Kalman-filter procedure.

Figure 3:
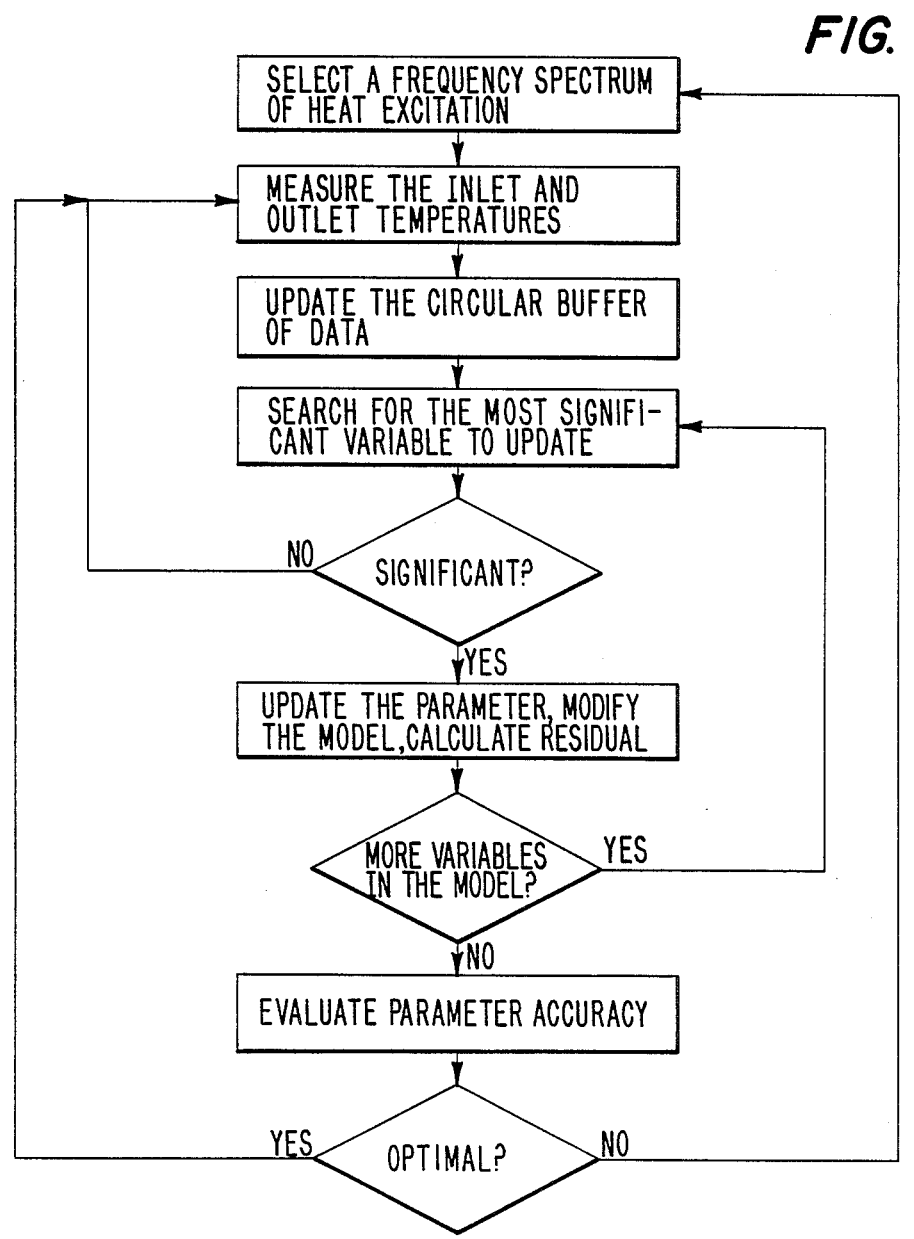
FIG. 3 illustrates a flowchart of the sequential updating performed in accordance with the present invention.

The Kalman-filter parameter identification is recursive, as a moving data window with a fixed size moves along with the sampling of temperatures. The regression is sequential, meaning that only parameters or model terms that show significant changes, will be subject to updating and identification. The update is performed when a set of data are collected, say every minute or five minutes. The sequential updating is performed in a computer program software, the general function of which is illustrated by the schematic flowchart portrayed in FIG. 3.

The principle of the parameter estimation is based on three loops. The two inner loops select the term in the ARMA model with the strongest correlation to the residual of the model, the idea being that the variable with the strongest correlation will have the maximum ability to explain an eventual systematic error in the residual, if there are no more variables in the model (the second inner loop), then the iterative loops for parameter update are terminated, and a new cycle of measurements is started. The statistical significance test is a standard F-test based on the least square of the residual of the ARMA model.

The third outer loop, determines the actual heat excitation in order to optimize the parameter accuracy. The objective function for this optimization is the determinant of the parameter covariance matrix. This optimization is much less frequent.

The actual details of the programming of a computer interfacing with the coldfinger to solve the various abovenoted equations would be readily apparent to a skilled programmer and it is noted that programs for solving the types of equations noted above utilizing known approximation techniques are of course known to skilled programmers and accordingly, a detailed description of such programs has been omitted for the sake of brevity.

The ARMA-model approximation to the heat diffusion dynamics makes it possible to estimate both the bulk temperature, the bath heat transfer coefficient and the solid/liquid interface equilibrium temperature.

The ARMA-model approach shows that a measurement of the air flowrate is not necessary. The ratio between the coldfinger heat capacity and the air flow rate is a parameter estimated from the time varying temperatures in and out of the coldfinger. This is a major saving in the instrument cost.

The ARMA-model estimator concentrates on the bath parameters and leaves all others as secondary variables, as for example the ratio betwen the crust heat conductivity, and the crust thickness, and the ratio betwen thermometer heat capacity and air flow rate. Those variables are not really of great interest to the operators of the bath.

The data processing suggested for the ARMA-model estimator is a well proven technique that has reached a mature state of stability. The sequential approach to regression is being experimented with in another industry with extremely promising performance.

Figure 5:
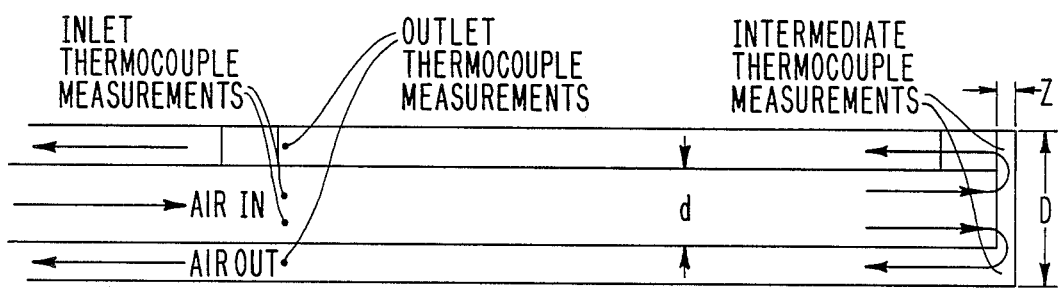
FIG. 5 illustrates another embodiment of a simplified coldfinger for use in accordance with the present invention.

FIG. 5 illustrates another alternative embodiment which the inventor has found to be simple to construct and which is advantageous in that it will operate both by fluctuating the air flow or air inlet temperature between maximum and minimum levels or by maintaining a steady state air flow and inlet temperature when the coldfinger is utilized in applications in which there are no fast parameter changes.

As illustrated in FIG. 5, the coldfinger consists of a closed outer hollow cylindrical cylinder and an open hollow cylindrical cylinder which is placed within the outer cylinder.

As in the other embodiments, fins located between the outer and inner cylinders maintain the position of the inner cylinder within the outer cylinder.

Unlike the earlier embodiments, in addition to providing temperature sensors (e.g.—thermocouples) at both the air or gas inlet to the inner cylinder and the air or gas outlet of the outer cylinder, intermediate temperature sensors are disposed at the interface between the outlet of the inner cylinder and the inlet of the outer cylinder.

In terms of the relative dimensions and placement of the inner and outer cylinders, the inventor has found that the ratio between the diameters of the inner and outer cylinders should follow the following equation:

$$D^2/d^2=2$$

wherein D and d are the respective diameters of the outer and inner cylinders.

In addition, it has been found that the optimum distance Z between the ends of the inner and outer cylinders should be made equal to d/4.

As in the other embodiments, the solid interface temperature (liquidus) may be estimated by a standard steady state parameter estimation technique (e.g.—leased squares) or by a standard dynamic parameter estimation technique (e.g.—KALMAN filter).

The equations for such a mathematical model are noted below in which the $^b$ refers to the bottom (that is—end) of the outer cylinder and the $^i$ refers to the inlet to the inner cylinder and the $^o$ refers to the outlet of the larger cylinder. In addition, the temperature $T_1$ refers to the inner cylinder temperature while the temperature $T_2$ refers to the outer cylinder temperature while the temperature $T_s$ refers to the surface temperature to be measured and the symbol C refers to a heat capacity while the symbol U refers to a heat transport function.

Steady state:

$$dT_1/dx = [U_1 A_1/(w_g c_p)](T_2 - T_1)$$

$$dT_2/dx = [U_2(x) A_2/(w_g c_p)](T_2 - T_s) - [U_1 A_1/(w_g c_p)](T_2 - T_1)$$

$$dQ/dx = 0 = d\{[U_2(x)A_2/(w_g c_p)](T_2 - T_s)\}/dx$$
$$-> d\{\ln(U_2(x))\}/dx = -d\{\ln(T_2 - T_s)\}/d_x$$

Parameters to be estimated by a steady state solution of the differential equations:

$$p_1 = U_1 A_1/(w_g c_p); \; p_2 = U_2(x)A_2/(w_g c_p); \; p_3 = T_s;$$

Boundary conditions are used as least square residuals:

$$e_1 = T_1(0) - T_i; \; e_2 = T_1(1) - T_b; \; e_3 = T_2(1) - T_b;$$
$$e_4 = T_2(0) - T_o;$$

Dynamic state:

$$dT_1/dx = [U_{1,1} A_{1,1}/(w_g c_p)](T_{1,1} - T_1)$$

$$dT_2/dx = [U_{2,1}(x)A_{2,1}/(w_g c_p)](T_2 - T_{2,2}) - [U_{1,2}A_{1,2}/(w_g c_p)](T_2 - T_{1,1})$$

$$d(T_{1,1} + T_{2,2})/dt = C_1\{[U_{1,2}A_{1,2}/(w_g c_p)](T_2 - T_{1,1}) - [T_{1,1}A_{1,1}/(w_g c_p)](T_{1,1} - T_1)\}$$

$$dT_{2,2}/dt = C_2\{[U_{2,2}(x)A_{2,2}/(w_g c_p)](T_s - T_{2,2}) - [U_{2,1}(x)A_{2,1}/(w_g c_p)](T_2 - T_{2,2})\}$$

Parameters to be estimated by a dynamic state solution of the differential equations:

$$p_1 = U_{1,1}A_{1,1}/(w_g c_p); \; p_2 = U_{1,2}A_{1,1}/(w_g c_p);$$
$$p_3 = U_{2,1}(1)A_{2,1}/(w_g c_p);$$

$$p_4 = U_{2,2}(1)A_{2,2}/(w_g c_p); \; p_5 = C_1; \; p_6 = C_2; \; p_7 = T_s;$$

Steady state profiles are used for the heat transmission coefficients:

$$d\{\ln(U_{2,2}(x))\}/dx = -d\{\ln(T_s - T_{2,2}(x))\}/dx$$

$$d\{\ln(U_{2,1}(x))\}/dx = -d\{\ln(T_{2,2}(x) - T_2(x))\}/dx$$

Boundary conditions are used as least square residuals:

$$e_1(t) = T_1(0,t) - T_i; \; e_2(t) = T_1(1,t) - T_b;$$
$$e_3(t) = T_2(1,t) - T_b; \; e_4(t) = T_2(0,t) - T_o;$$

Figure 6:
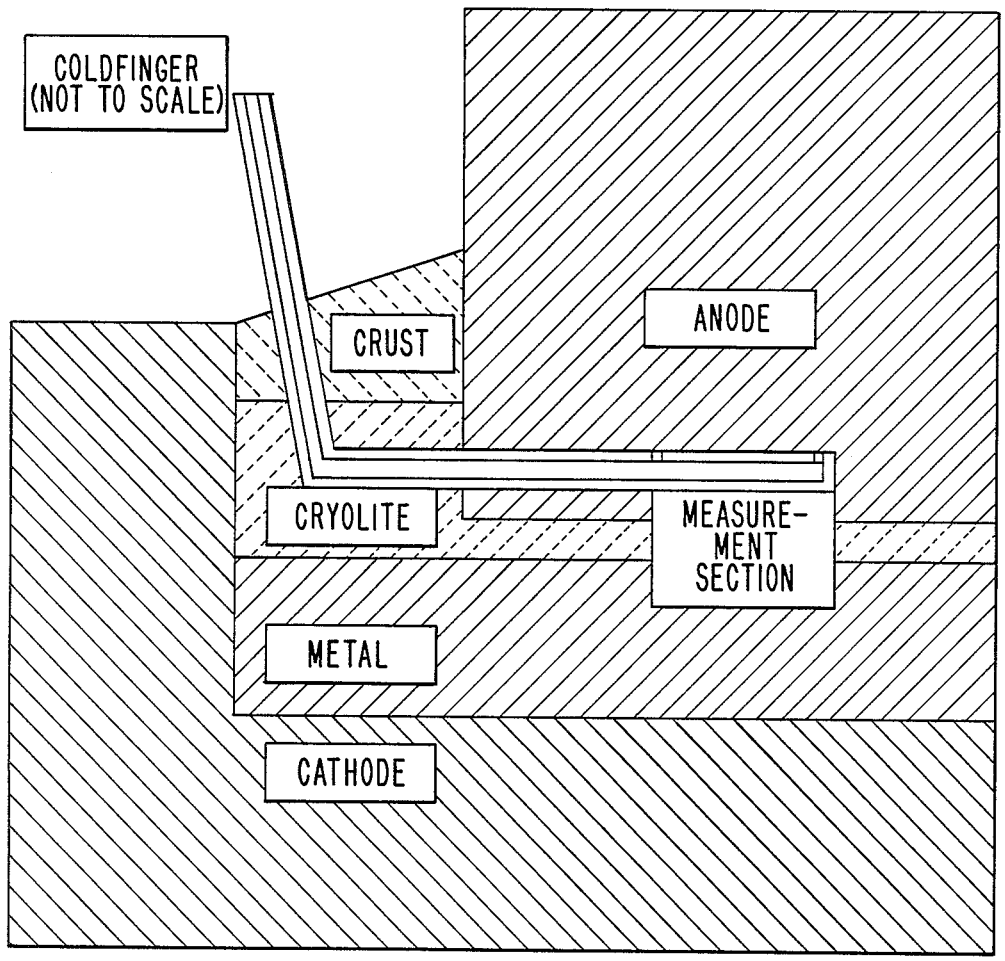
FIG. 6 illustrates the arrangement of a coldfinger within a metal/Cryolite bath.

FIG. 6 illustrates the use of a coldfinger in an aluminum reduction cell in which the measuring section of the coldfinger is the end portion of a longer stick mounted above and parallel to the aluminum metal level.

I claim:

1. An apparatus for indirectly measuring a solid-liquid interface equilibrium temperature comprising:
    a coldfinger arrangement disposed within the liquid whose solid-liquid interface equilibrium temperature is to be measured, said coldfinger comprising a pair of substantially concentric and substantially cylindrical members arranged one within the other so as to have an outer member and an inner member and a space therebetween; said outer and inner members having closed ends and first and second apertures arranged to form a closed system wherein when a gas is fed through said first aperture, said gas flows through said inner member and said space between said inner and outer members and exits said second aperture;
    a means for providing a flow of gas to said first aperture via a gas line;
    a heating means arranged within said gas line for raising the temperature of said gas by supplying heat thereto;
    another gas line connected to said second aperture for exhausting said gas exiting from said second aperture;
    a temperature measuring means for measuring an average gas temperature within said space of said coldfinger and a differential temperature measuring means for measuring the difference in temperature between the gas entering said coldfinger via said gas line and the gas exiting said coldfinger via said another gas line;
    a means for varying the dynamic excitation of the heat flux flowing through said coldfinger by varying in a time varying fashion either the amount of heat supplied by said heating means to said gas or the amount of gas flowing through said gas line;
    wherein the solid-liquid interface equilibrium temperature is determined on the basis of the respective temperatures measured by the temperature measuring means and differential temperature measuring means and the specific parameters of the gas and the solid and the liquid and the gas flowrate and the dimensions of the coldfinger.

2. An apparatus as recited in claim 1, wherein the solid and liquid whose solid-liquid interface equilibrium temperature is to be measured respectively comprise solid and liquid cryolite and wherein said gas comprises air.

3. An apparatus as recited in claim 1, wherein said inner member is venturi-shaped.

4. An apparatus as recited in claim 2, wherein said inner member is venturi-shaped.

5. A method for indirectly measuring a solid-liquid interface equilibrium temperature comprising the steps of:
    providing a coldfinger arrangement disposed within the liquid whose solid-liquid interface equilibrium temperature is to be measured, the coldfinger including a pair of substantially concentric and substantially cylindrical members arranged one within the other so as to have an outer and an inner member and a space therebetween; the outer and inner members having closed ends and first and second apertures arranged to form a closed system wherein when a gas is fed through the first aperture, the gas flows through the inner member and the space between the inner and outer members and exits the second aperture;
    providing a flow of gas to the first aperture via a gas line;
    raising the temperature of the gas within the gas line using a heating means for supplying heat thereto;

exhausting the gas exiting from the second aperture via another gas line connected to the second aperture;

measuring an average gas temperature within the space of the coldfinger by a temperature measuring means and measuring the difference in temperature between the gas entering the coldfinger via the gas line and the gas exiting the coldfinger via another gas line with a differential temperature measuring means;

varying the dynamic excitation of the heat flux flowing through the coldfinger by varying in a time varying fashion either the amount of heat supplied by the heating means to the gas or the amount of gas flowing through the gas line;

determining the solid-liquid interface equilibrium temperature on the basis of the respective temperatures measured by the temperature measuring means and the differential temperature measuring means and the specific parameters of the gas and the solid and the liquid and the gas flowrate and the dimensions of the coldfinger.

6. A method as recited in claim 5, wherein the solid and liquid whose solid-liquid interface equilibrium temperature is to be measured respectively comprise solid and liquid cryolite and wherein the gas provided comprises air.

7. A method as recited in claim 5, wherein a venturi-shaped member is provided as the inner member of the coldfinger arrangement.

8. A method as recited in claim 6, wherein a venturi-shaped member is provided as the inner member of the coldfinger arrangement.

9. An apparatus for indirectly measuring a solid-liquid interface equilibrium temperature comprising:

a coldfinger arrangement disposed within the liquid whose solid-liquid interface equilibrium temperature is to be measured, said coldfinger comprising a substantially cylindrical member having a space therein and arranged so as to have closed ends and first and second apertures arranged to form a closed system wherein when a gas is fed through said first aperture, said gas flows within said space and exits said second aperture;

a means for providing a flow of gas to said first aperture via a gas line;

a heating means arranged within said gas line for raising the temperature of said gas by supplying heat thereto;

another gas line connected to said second aperture for exhausting said gas exiting from said second aperture;

a temperature measuring means for measuring an average gas temperature within said space of said coldfinger and a differential temperature measuring means for measuring the difference in temperature between the gas entering said coldfinger via said gas line and the gas exiting said coldfinger via said another gas line;

a means for varying the dynamic excitation of the heat flux flowing through said coldfinger by varying in a time varing fashion either the amount of heat supplied by said heating means to said gas or the amount of gas flowing through said gas line;

wherein the solid-liquid interface equilibrium temperature is determined on the basis of the respective temperatures measured by the temperature measuring means and differential temperature measuring means and the specific parameters of the gas and the solid and the liquid and the gas flowrate and the dimensions of the coldfinger.

10. An apparatus as recited in claim 9, wherein the solid and liquid whose solid-liquid interface equilibrium temperature is to be measured respectively comprise solid and liquid cryolite and wherein said gas comprises air.

11. A method for indirectly measuring a solid-liquid interface equilibrium temperature comprising the steps of:

providing a coldfinger arrangement disposed within the liquid whose solid-liquid interface equilibrium temperature is to be measured, the coldfinger including a substantially cylindrical member having a space therein and arranged so as to have closed ends and first and second apertures forming a closed system wherein when a gas is fed through the first aperture, the gas flows through the space therein and exits the second aperture;

providing a flow of gas to the first aperture via a gas line;

raising the temperature of the gas within the gas line using a heating means for supplying heat thereto;

exhausting the gas exiting from the second aperture via another gas line connected to the second aperture;

measuring an average gas temperature within the space of the coldfinger by a temperature measuring means and measuring the difference in temperature between the gas entering the coldfinger via the gas line and the gas exiting the coldfinger via another gas line with a differential temperature measuring means;

varying the dynamic excitation of the heat flux flowing through the coldfinger by varying in a time varying fashion either the amount of heat supplied by the heating means to the gas or the amount of gas flowing through the gas line;

determining the solid-liquid interface equilibrium temperature on the basis of the respective temperatures measured by the temperature measuring means and the differential temperature measuring means and the specific parameters of the gas and the solid and the liquid and the gas flowrate and the dimensions of the coldfinger.

12. A method as recited in claim 11, wherein the solid and liquid whose solid-liquid interface equilibrium temperature is to be measured respectively comprise solid and liquid cryolite and wherein the gas provided comprises air.

13. An apparatus for indirectly measuring a solid-liquid interface equilibrium temperature comprising:

a coldfinger arrangement disposed within the liquid whose solid-liquid interface equilibrium temperature is to be measured, said coldfinger comprising an outer member and an inner member and a space therebetween; said outer member having a closed end and said inner member having an open end disposed towards said closed end of said outer member, and first and second apertures arranged to form a closed system wherein when a gas is fed through said first aperture, said gas flows through said inner member and said space between said inner and outer members and exits said second aperture;

a means for providing a flow of gas to said first aperture via a gas line;

another gas line connected to said second aperture for exhausting said gas exiting from said second aperture;

a temperature measuring means for measuring cross section average temperatures of both a gas inlet cross section of said inner member, and a gas outlet of said inner member, which is also an average temperature of a gas inlet to said outer member annulus cross section, and for measuring an average temperature of a gas outlet from said outer member annulus cross section;

a means for controlling the heat flux flowing through said coldfinger by controlling the amount of heat supplied to said coldfinger by said gas or by controlling the amount of gas flowing through said gas line;

wherein the solid-liquid interface equilibrium temperature is determined on the basis of the respective temperatures measured by said temperature measuring means and the specific estimated parameters of the gas and the solid and the liquid and the gas flowrate and the dimensions of the coldfinger.

14. An apparatus as recited in claim 13, wherein the solid and liquid whose solid-liquid interface equilibrium temperature is to be measured respectively comprise solid and liquid cryolite and wherein said gas comprises air.

15. A method for indirectly measuring a solid-liquid interface equilibrium temperature comprising the steps of:

providing a coldfinger arrangement disposed within the liquid whose solid-liquid interface equilibrium temperature is to be measured, the coldfinger including an outer and an inner member and a space therebetween; said outer member having a closed end and said inner member having an open end disposed towards said closed end of said outer member, and first and second apertures arranged to form a closed system wherein when a gas is fed through the first aperture, the gas flows through the inner member and the space between the inner and outer members and exits the second aperture;

providing a flow of gas to the first aperture via a gas line;

exhausting the gas exiting from the second aperture via another gas line connected to the second aperture;

measuring cross section average gas temperatures of both a gas inlet cross section of the inner member and a gas outlet of the inner member, which is also an average temperature of a gas inlet to the outer member annulus cross section, and measuring an average temperature of a gas outlet from the outer member annulus cross section;

controlling the heat flux flowing through the coldfinger by varying the amount of heat supplied to the coldfinger by the gas or by controlling the amount of gas flowing through the gas line;

determining the solid-liquid interface equilibrium temperature on the basis of the respective temperatures measured and the specific estimated parameters of the gas and the solid and the liquid and the gas flowrate and the dimensions of the coldfinger.

16. A method as recited in claim 15, wherein the solid and liquid whose solid-liquid interface equilibrium temperature is to be measured respectively comprise solid and liquid cryolite and wherein the gas provided comprises air.

* * * * *